United States Patent [19]
Singer et al.

[11] Patent Number: 5,823,193
[45] Date of Patent: Oct. 20, 1998

[54] DENTAL APPLIANCE FOR ALLEVIATING SNORING AND PROTECTING TEETH FROM BRUXISM

[76] Inventors: Gary H. Singer, 1717 W. Chester Pike, Havertown, Pa. 19083; Carl Erwin Misch, 410 Claremount, Dearborn, Mich. 48124; Neil R. Gottehrer, 202 Clwyd Rd., Bala Cynwyd, Pa. 19004

[21] Appl. No.: 789,641

[22] Filed: Jan. 27, 1997

[51] Int. Cl.⁶ .................................................. A61F 5/56
[52] U.S. Cl. ...................... 128/848; 128/859; 128/861; 602/902
[58] Field of Search ............................... 128/846, 848, 128/859–862; 433/6; 602/902

[56] References Cited

U.S. PATENT DOCUMENTS

| | | | |
|---|---|---|---|
| 5,328,362 | 7/1994 | Watson | 128/861 |
| 5,365,945 | 11/1994 | Halstrom | 128/848 |
| 5,499,633 | 3/1996 | Fenton | 128/848 |
| 5,562,106 | 10/1996 | Heeke et al. . | |
| 5,566,683 | 10/1996 | Thornton . | |
| 5,642,737 | 7/1997 | Parks | 128/848 |

OTHER PUBLICATIONS

An American Sleep Disorders Association Review; Oral Appliances for the Treatment of Snoring and Obstructive Sleep Apnea: A Review; Wolfgang Schmidt–Nowara, Alan Lowe, Laurel Wiegand, Rosalind Cartwright, Francisco Perez–Guerra and Stuart Menn; vol. 18, No. 6, 1995, pp. 501–510.

An American Sleep Disorders Association Report; Practice Parameters for the Treatment of Snoring and Obstructive Sleep Apnea with Oral Appliances; vol. 18, No. 6, 1995, pp. 511–513.

Dental Appliances for the Treatment of Snoring and Obstructive Sleep Apnea; Alan A. Lowe; Chapter 69, pp. 722–735.

*Primary Examiner*—Michael A. Brown
*Attorney, Agent, or Firm*—Brooks & Kushman, P.C.

[57] ABSTRACT

A single dental appliance that both alleviates snoring and protects teeth from bruxism. The appliance (10) has an upper section (12) which is mounted on the upper jaw. Opposing the upper section (12) is a lower section (14) which is mounted on the lower jaw. Both the upper and lower section have an anterior region (16, 18) and two posterior regions (20, 22; 24, 26). A hard outer shell (32, 34) secures in a soft inner liner (28, 30) which conforms with the teeth and cushions the jaw against impact forces. The hard outer shell (32, 34) serves to protect the teeth against grinding. The combination of the liner and the shell distribute forces associated with grinding.

15 Claims, 2 Drawing Sheets

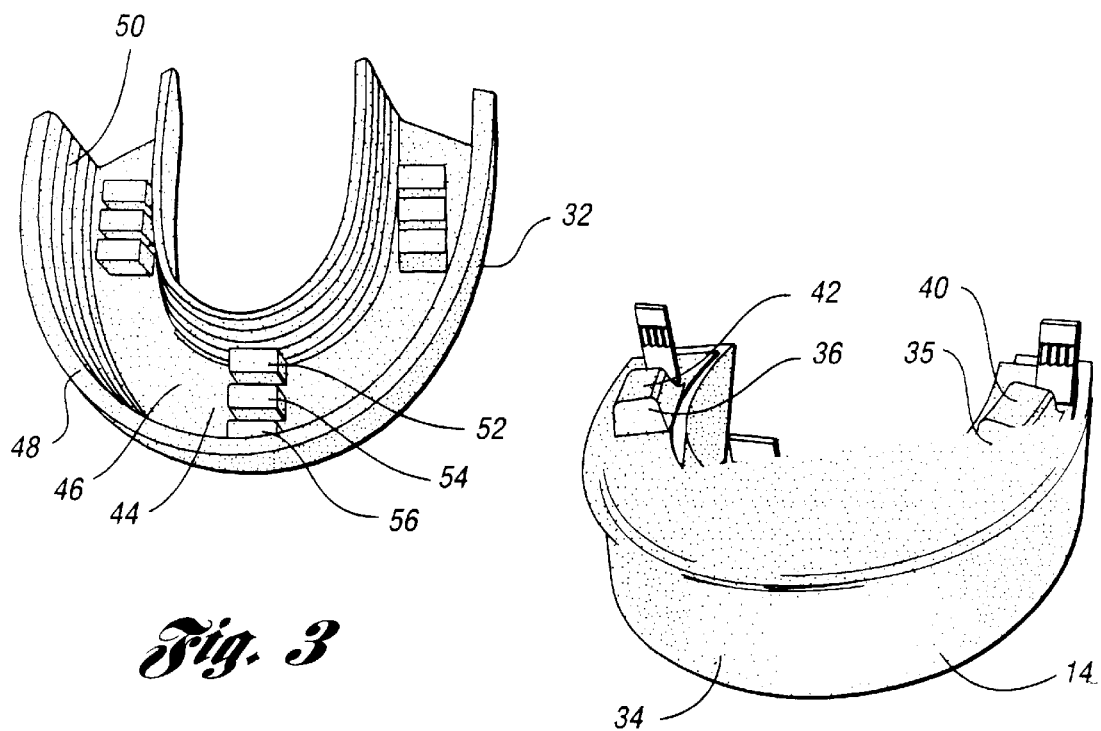
Fig. 3
Fig. 4
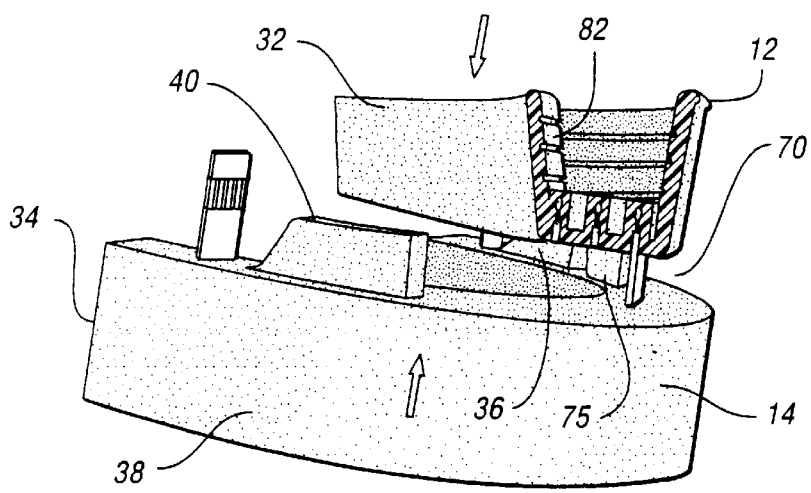
Fig. 5
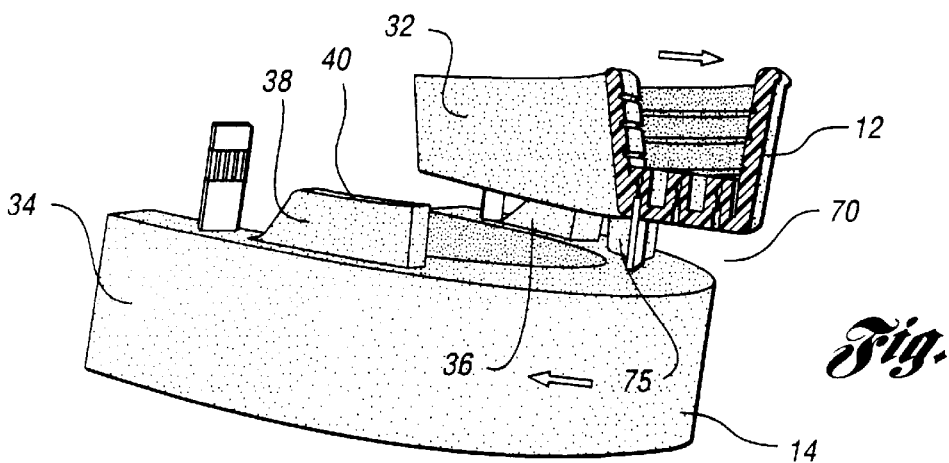
Fig. 6

DENTAL APPLIANCE FOR ALLEVIATING SNORING AND PROTECTING TEETH FROM BRUXISM

TECHNICAL FIELD

This invention relates to a single dental appliance which both protects teeth from bruxism and alleviates snoring.

BACKGROUND OF THE INVENTION

1. Bruxism

Bruxism is the vertical and horizontal, non-functional grinding of teeth. The forces involved often exceed the normal physiologic masticatory loads (up to 1,000 psi). Bruxism may adversely affect teeth, muscles and joints, or all three. Such adverse effects may occur while the patient is awake or asleep.

Use of a bite guard is helpful for many bruxism patients. A bite guard, in one form, resembles a semi-transparent mouth guard that a boxer or football player might wear to protect his teeth. The guard is placed over the teeth to protect them from grinding.

Most bite guards in dentistry are made of hard plastic. Although hard plastic is more resilient than teeth, it is not as resilient as a soft, rubber-like, elastomeric material. Thus, most conventional hard acrylic bite guards are custom made. The procedure requires impressions to be made and involves various time-consuming and expensive laboratory steps.

Though athletic mouth guards are resilient, as are some guards to protect the teeth from clenching, they wear rapidly in patients who grind their teeth.

2. Snoring

About 40–60 million Americans may be chronic snorers, according to some estimates. About half of them may suffer from sleep apnea, a breathing disorder that interrupts sleep and prevents the body from receiving sufficient oxygen.

A normal airway is about the diameter of a pencil. Snoring typically occurs when a patient sleeps on his back. The sound is induced by inrushing and outrushing air vibrating against the uvula, a small conical fleshy tissue that hangs from the middle of the soft palate. In sleep apnea, the muscles of the soft palate at the base of the tongue and the uvula relax and sag. This obstructs the airway and makes breathing labored and noisy.

One of the inventors has modified a conventional mouth guard, custom fitted by the dentist to the patient's bite, that forces the patient to breathe through his nose. It causes the lower jaw to move forwardly. This alters the position of the uvula and the muscles of the soft palate at the base of the tongue so that airway blockage is avoided or minimized. However, the patient cannot adjust this device without professional assistance.

U.S. Pat. No. 5,566,683 discloses an apparatus for preventing snoring. This reference, discloses a ramp adapted to fit in receiving grooves, the ramp urging the user's lower jaw to extend forwardly.

SUMMARY OF THE INVENTION

One object of the present invention is to provide in a single invention a dental appliance which alleviates snoring problems while protecting the teeth from bruxism, while being able to readily be adjusted by the patient without professional help.

Another object of the present invention is to combine hard material on the outside of a bite guard to resist grinding and distribute forces with a soft resilient material on the inside to decrease the impact of the force.

Yet another object is to provide a bite guard that can be fabricated directly in the patient's mouth, thereby eliminating intraoral impressions, laboratory procedures, time and cost.

A further object of the invention is to provide a bite guard that has hard anterior inclines which separate the posterior teeth when the patient grinds on the anterior teeth. Such a guard decreases the amount of muscle contraction of the two major muscles used for grinding the teeth.

Accordingly, the invention is a dental appliance which comprises an upper section mountable on the upper jaw. Opposing the upper section is a lower section mountable on the lower jaw. Each section has a hard outer shell which accommodates an inner liner.

In one embodiment, female guides are formed in the upper section which receive male posts extending upwardly from the lower section. Registration of the posts with the guides enables the upper and lower sections to be adjustably positioned in an anterior-posterior relation. Such registration also provides an open and unobstructed airway space between the upper and lower sections, thereby permitting unimpeded breathing.

BRIEF DESCRIPTION OF THE DRAWINGS

A more complete appreciation of the invention and many of the attendant advantages thereof may be readily obtained by reference to the following detailed description when considered with the accompanying drawing in which like reference characters indicate corresponding parts in all the views, wherein:

In FIG. 2, the upper section is depicted in the lower portion to illustrate features (described later) of the upper section which are not apparent from FIG. 1 alone;

FIG. 3 is a perspective view of the inside of a hard outer shell of the upper section;

FIG. 4 is a perspective view of the lower section;

FIG. 5 is a side perspective view of the lower and upper sections, wherein the upper section is partially broken away, and in which the upper and lower sections lie in a first posterior-anterior position; and FIG. 6 is another side perspective view of the lower section and of the upper section depicted in FIG. 5, in which the upper and lower sections lie in a second posterior-anterior position.

DETAILED DESCRIPTION OF THE PREFERRED EMBODIMENT

Figure 1:
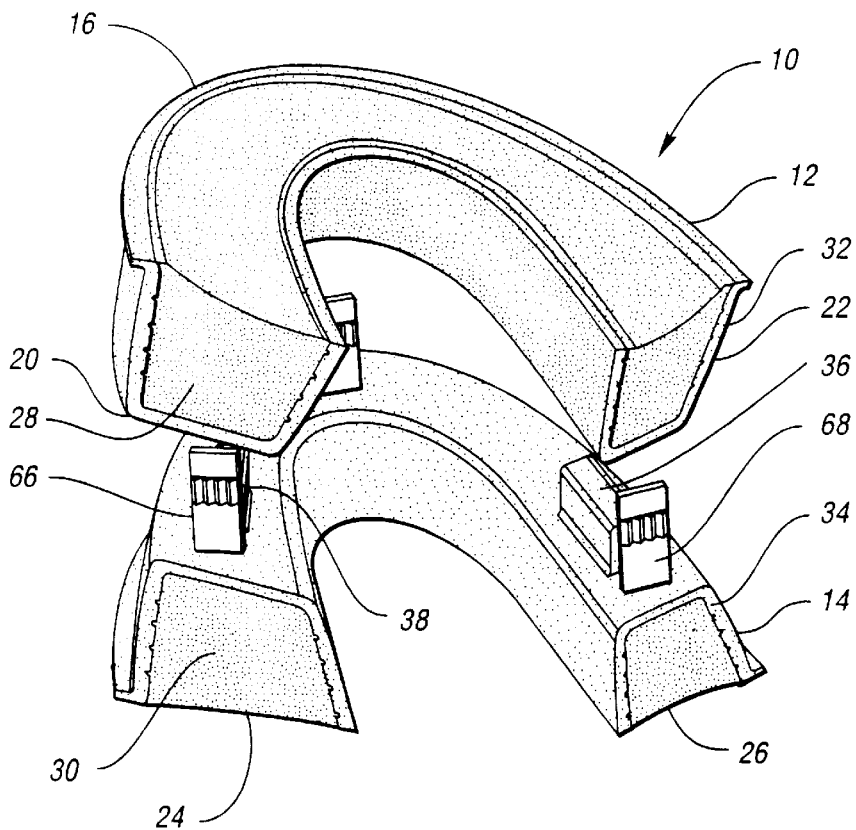
FIG. 1 is a perspective, exploded view of a dental appliance including an upper section and a lower section.

Turning first to FIG. 1 of the drawing, the invention discloses a dental appliance 10 for alleviating snoring and protecting teeth from bruxism. The appliance 10 includes an upper section 12 which is mountable on the upper jaw. Opposing the upper section 12 is a lower section 14 mounted on the lower jaw. Each of the lower and upper sections 12, 14 has one anterior region 16, 18 and two posterior regions, 20, 22; 24, 26. Each section also has a soft inner liner 28, 30 which conforms with the teeth and cushions the jaw against impact forces. A hard outer shell 32, 34 is provided on each of the upper and lower sections 12, 14 to resist grinding. The hard outer shell 32, 34 secures the inner liner, protects the teeth, and distributes forces associated with grinding.

The embodiment depicted in FIG. 1 includes a pair of bite stops 36, 38 provided in the hard outer shell 34. In that embodiment, one bite stop 36 is provided in the posterior region 26 and one bite stop 38 is provided in the posterior region 24 of the lower section 14.

Figure 2:
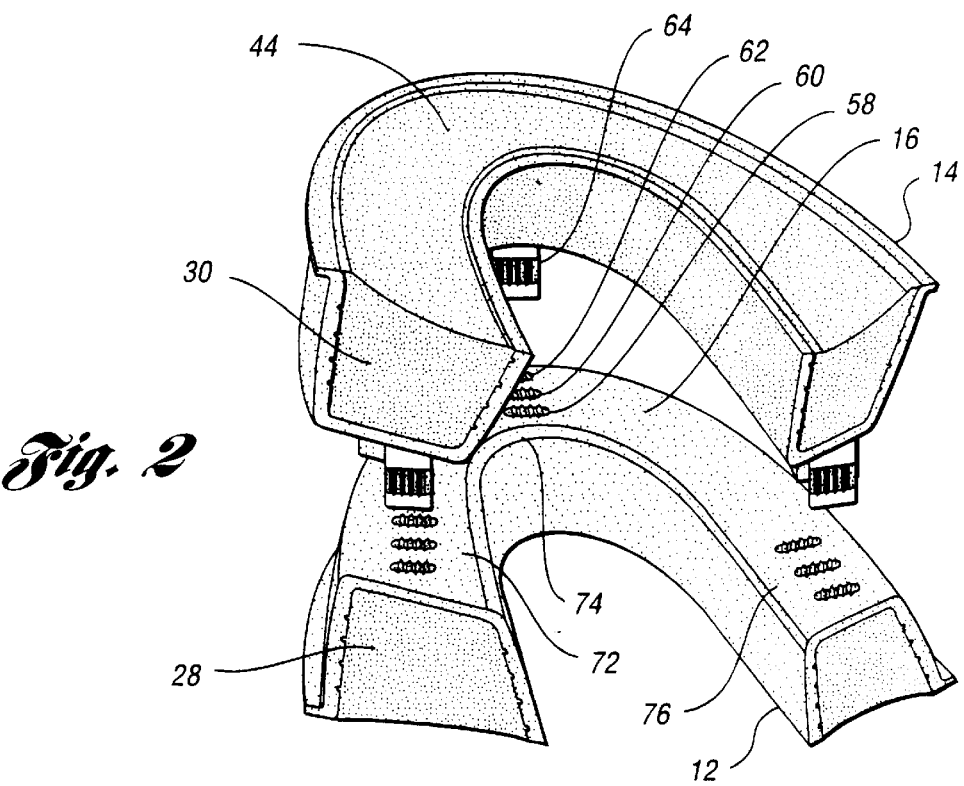
FIG. 2 is an inverted view of the device depicted in FIG. 1.

FIG. 2 is an inverted view of the embodiment depicted in FIG. 1. Details of the upper section 12 (otherwise substantially hidden from the view of FIG. 1) are disclosed. In FIGS. 2–3, at least one of the sections, and preferably the upper section 12 includes a plurality of spaced housings 52, 54, 56 (see FIG. 3) for defining female guides 58, 60, 62 (see FIG. 2). Each female guide is adapted to receive a single male post 64, 66, 68 extending from the facing section. This configuration enables the upper and lower sections 12, 14 to be adjustably positioned in an anterior-posterior relation. When the posts and the guides are seated, the spaced apart relationship of the upper and lower sections 12, 14 define an open and unobstructed airway space 70 (see FIGS. 5, 6) between the upper and lower sections 12, 14, thereby permitting unimpeded breathing. In the preferred embodiment shown, each of the female guides is formed in the upper section 12.

As depicted, the female guides comprise at least three sets 72, 74, 76 (FIG. 2) of guides. One set 74 is located at the anterior region 16. Two sets are located at the posterior regions of the upper section 12.

As shown in FIG. 2, each set of the plurality of female guides comprises at least three guide orifices 58, 60, 62. In that embodiment, the female guides in each of the sets are aligned in an anterior-posterior relation to permit front and rear bite adjustments.

Turning now to FIGS. 4–6, the embodiment depicted has an upper section 12 with two anterior bite stops 78. A corresponding bite stop does not appear because it depends downwardly from the hard outer shell of the upper section 12 which is broken away from the view of FIGS. 5–6. In the lower section 14, there are two posterior bite stops 36, 38, provided in the hard outer shell 34 so that masticatory forces are distributed through the hard shells. Thus, uneven forces in the soft inner liners (not shown in FIGS. 5–6) are distributed more uniformly.

Turning now to FIGS. 4–6, the anterior bite stops 36, 38 extending upwardly from the lower section 14 define anterior inclines 40, 42 which separate the posterior teeth when the mandible protrudes during grinding between the anterior teeth. In this way, associated muscle contraction is decreased. Forces exerted by the posterior large muscles are thereby reduced, thus alleviating stress created during grinding.

Each figure, except FIG. 4, discloses that each hard outer shell 32, 34 includes a U-shaped or arch-like structure 44 that defines an inner channel 46 (see especially FIG. 3) which receives the soft inner liner (FIGS. 1–2). The inner channel has a wall 48 including undercut ribs 82 (FIG. 5) for securing the soft inner liner within the hard outer shell. Such ribs (and any equivalent structure) serve to engage the soft inner liner and secure it in relation to the hard outer shell. Additional securing devices could be used, including cooperating posts and recesses, various adhesives, and the like.

When the upper and lower sections 12, 14 are secured by the registration of the male posts within the female guides, there is a space between the lower posterior stabilizing block 38 and the upper section 12. The space allows the lower jaw to move forward into two more positions (FIGS. 4–6).

The upper portion alone of FIG. 1 depicts an alternate embodiment of the invention. In that embodiment, the dental appliance is used primarily for protecting teeth from bruxism without the requirement for an opposing lower section. In this alternate embodiment, the dental appliance includes an upper section 12 mountable on the upper jaw. In the upper section 12, there is a hard outer shell and a soft inner liner secured within the hard outer shell. The hard outer shell serves to protect the teeth against grinding, while the soft inner liner helps distribute forces associated therewith. If desired in the alternate embodiment, at least one anterior bite stop is provided. In another embodiment, at least two anterior bite stops are provided.

To provide design flexibility, in this embodiment, the dental appliance may include a plurality of spaced housings for providing female guides adapted to receive male posts extending from a lower section if and when installed.

The disclosed device can be fabricated directly in the patient's mouth. This eliminates intraoral impressions, laboratory procedures, time and associated cost.

It will be appreciated that the outer shell may be fabricated with different general dimensions to accommodate the vast majority of jaw sizes Preferably, the shell is made of a hard acrylic-like material. One suitable material from which the hard outer shell may be prepared is LEXAN resin HP3-111, made by General Electric. Other materials such as a methylmethacrylate or a polycarbonate resin may be suitable. Alternative comparable and suitable materials can be used.

The soft resilient material of which the inner liner is made may be softened by heat or light. Once soft, the hard outer shell is placed over the teeth and indexes the surface of the teeth. The soft resilient material then becomes set over time or with a catalyst of light or chemical. Once the soft inner liner is set, the occlusion or bite of the patient may be adjusted. One suitable type of filler material is known as Alvax, an ethylene-vinyl acetate copolymer resin, made by DuPont. If a material such as Alvax is used, the soft inner liner 28, 30 may be heated to a temperature of about 150° F. using a microwave oven or by heating in hot water, thereby imparting a deformable characteristic to the liner material. In use, the hard outer shell is then inserted before the patient is invited to bite down. In this way, the soft material is deformed and conforms to the shape of the user's teeth. The hard outer shell and its liner are then removed and cooled, thereby setting the material into a pattern of the user's teeth.

The disclosed materials are within the purview of those of ordinary skill in prescribing dental appliances. Other materials may be used which would thus fall within the intended scope of the claimed invention.

While the best mode for carrying out the invention has been described in detail, those familiar with the art to which this invention relates should recognize various alternative designs and embodiments for practicing the invention as defined by the following claims.

What is claimed is:

1. A dental appliance for alleviating snoring and protecting teeth from bruxism, comprising:

an upper section mountable upon the upper jaw; and a lower section mountable on the lower jaw opposing the upper section, each section having an anterior region and two posterior regions;

an inner liner which conforms with the teeth and cushions the jaw against impact forces; and a hard outer shell to resist grinding, which secures the inner liner and distributes forces associated with grinding, at least one of the lower and upper sections being provided with at least one posterior bite stop disposed in the hard outer shell.

2. The dental appliance of claim 1, wherein the lower section has inclines formed in the bite stop which separate the posterior teeth when the mandible protrudes during grinding between the anterior teeth, thereby decreasing associated muscle contraction and decreasing force exerted by the posterior large muscles and reducing stress created during grinding.

3. The dental appliance of claim 1, wherein at least one of the upper and lower sections includes a plurality of spaced housings for defining female guides, one housing defining one female guide, each female guide being adapted to receive a male post extending from the other section, thereby enabling the upper and lower sections to be adjustably positioned in an anterior-posterior relation and for providing an open and unobstructed airway space between the upper and lower sections, thereby permitting unimpeded breathing.

4. The dental appliance of claim 3, wherein each of the plurality of female guides is formed in the upper section.

5. The dental appliance of claim 4, wherein the plurality of female guides comprises at least three sets of guides, one set being located at the anterior region and at least two sets being located at the posterior regions of the upper section.

6. The dental appliance of claim 5, wherein each set of the plurality of female guides comprises at least three guide orifices.

7. The dental appliance of claim 4, wherein the plurality of female guides comprises three sets of guides, one set being located at the anterior region, and two sets being located at the posterior regions of the upper section.

8. The dental appliance of claim 7, wherein each set of the plurality of female guides comprises three guide orifices.

9. The dental appliance of claim 7, wherein the plurality of female guides are aligned in an anterior-posterior relation to permit front and rear bite adjustment.

10. A dental appliance for alleviating snoring and protecting teeth from bruxism, comprising:
    an upper section mountable upon the upper law; and
    a lower section mountable on the lower law opposing the upper section, each section having an anterior region and two posterior regions;
    an inner liner which conforms with the teeth and cushions the law against impact forces;
    a hard outer shell to resist grinding, which secures the inner liner and distributes forces associated with grinding;
    wherein each hard outer shell comprises:
    a U-shaped structure that defines an inner channel which receives the inner liner, the inner channel having a wall including undercut ribs for securing the inner liner within the hard outer shell.

11. A dental appliance for alleviating snoring and protecting teeth from bruxism, comprising:
    an upper section mountable upon the upper law; and
    a lower section mountable on the lower law opposing the upper section, each section having an anterior region and two posterior regions;
    an inner liner which conforms with the teeth and cushions the law against impact forces;
    a hard outer shell to resist grinding, which secures the inner liner and distributes forces associated with grinding; wherein
    the upper section has at least two anterior bite stops provided in the hard outer shell; and
    the lower section has at least two posterior bite stops provided in the hard outer shell, so that masticatory forces are distributed through the hard shells and uneven forces in the inner liners are distributed more uniformly.

12. A dental appliance for protecting teeth from bruxism, consisting essentially of:
    an upper section mountable upon the upper jaw, the upper section having
    an anterior region and two posterior regions;
    an inner liner which conforms with the teeth and cushions the upper jaw against impact forces; and
    a hard outer shell which accommodates the inner liner to protect the teeth against grinding and distribute forces associated therewith.

13. The dental appliance of claim 12, further comprising at least one anterior bite stop.

14. The dental appliance of claim 12, further comprising at least two bite stops.

15. The dental appliance of claim 12, further comprising a plurality of spaced housings for defining female guides, one housing defining one female guide, adapted to receive male posts extending from a lower section to be installed.

* * * * *

UNITED STATES PATENT AND TRADEMARK OFFICE
CERTIFICATE OF CORRECTION

PATENT NO. : 5,823,193
DATED : October 20, 1998
INVENTOR(S) : GARY H. SINGER et al.

It is certified that error appears in the above-identified patent and that said Letters Patent is hereby corrected as shown below:

Column 5, Line 41, Claim 10, delete "law" and insert --jaw--.

Column 5, Line 42, Claim 10, delete "law" and insert --jaw--.

Column 5, Line 47, Claim 10, delete "law" and insert --jaw--.

Column 6, Line 11, Claim 11, delete "law" and insert --jaw--.

Column 6, Line 12, Claim 11, delete "law" and insert --jaw--.

Column 6, Line 16, Claim 11, delete "law" and insert --jaw--.

Signed and Sealed this

Twenty-seventh Day of July, 1999

*Attest:*

Q. TODD DICKINSON

*Attesting Officer*  *Acting Commissioner of Patents and Trademarks*